United States Patent
Horiuchi et al.

(10) Patent No.: US 12,219,969 B2
(45) Date of Patent: Feb. 11, 2025

(54) FERMENTED MILK AND METHOD FOR MANUFACTURING FERMENTED MILK

(71) Applicant: Meiji Co., Ltd., Tokyo (JP)

(72) Inventors: Hiroshi Horiuchi, Kanagawa (JP); Takefumi Ichimura, Kanagawa (JP); Nobuko Inoue, Kanagawa (JP); Nao Takagi, Kanagawa (JP)

(73) Assignee: Meiji Co., Ltd., Tokyo (JP)

( * ) Notice: Subject to any disclaimer, the term of this patent is extended or adjusted under 35 U.S.C. 154(b) by 213 days.

(21) Appl. No.: 17/730,669

(22) Filed: Apr. 27, 2022

(65) Prior Publication Data

US 2022/0248699 A1    Aug. 11, 2022

Related U.S. Application Data

(62) Division of application No. 16/652,068, filed as application No. PCT/JP2018/035502 on Sep. 25, 2018, now Pat. No. 11,344,040.

(30) Foreign Application Priority Data

Sep. 29, 2017  (JP) .................. 2017-189949

(51) Int. Cl.
    A23C 9/127     (2006.01)
    A23C 9/123     (2006.01)
    C12N 1/20      (2006.01)
    C12R 1/225     (2006.01)

(52) U.S. Cl.
    CPC .......... *A23C 9/1275* (2013.01); *A23C 9/1238* (2013.01); *A23V 2400/123* (2023.08); *C12N 1/205* (2021.05); *C12R 2001/225* (2021.05)

(58) Field of Classification Search
    CPC ............ A23L 27/82; A23L 19/09; A23L 27/60
    USPC ........................................... 426/650
    See application file for complete search history.

(56) References Cited

U.S. PATENT DOCUMENTS

| | | |
|---|---|---|
| 2012/0156327 A1 | 6/2012 | Robichon et al. |
| 2013/0266691 A1 | 10/2013 | Horiuchi |
| 2014/0057019 A1 | 2/2014 | Kawai |

(Continued)

FOREIGN PATENT DOCUMENTS

| | | |
|---|---|---|
| CN | 102870877 A | 1/2013 |
| JP | 2012-528582 A | 11/2012 |
| JP | 2016189709 A * | 11/2016 |

(Continued)

OTHER PUBLICATIONS

Translation of JP-2016189709-A (Year: 2016).*

(Continued)

*Primary Examiner* — Brent T O'Hern
(74) *Attorney, Agent, or Firm* — Renner, Otto, Boisselle & Sklar, LLP

(57) ABSTRACT

In a preparation step, raw material milk is prepared. In a lactose degradation step, at least part of lactose included in the prepared raw material milk is degraded using a lactose-degrading enzyme. The lactose concentration in the raw material milk in which lactose is degraded is not more than 2.5% by mass with respect to a total amount of the raw material milk. A lactic acid bacterium is added to the raw material milk in which at least part of lactose is degraded, and the raw material milk to which the lactic acid bacterium is added is fermented.

5 Claims, 1 Drawing Sheet

| | LACTIC ACID BACTERIUM STARTER | LACTOSE CONCENTRATION (% BY MASS) | CONTENT OF EPS (mg/kg) | COUNT OF LACTOBACILLUS BULGARICUS (×10⁷cfu/g) | COUNT OF STREPTOCOCCUS THERMOPHILUS (×10⁷cfu/g) |
|---|---|---|---|---|---|
| COMPARATIVE EXAMPLE1 | OLL1073R-1 STRAIN | 5 | 23.6 | 21.2 | 66.0 |
| INVENTIVE EXAMPLE1 | | 2.5 | 26.2 | 24.7 | 95.5 |
| INVENTIVE EXAMPLE2 | | 1 | 31.6 | 25.3 | 103.5 |
| INVENTIVE EXAMPLE3 | | 0 | 36.5 | 37.9 | 80.5 |
| COMPARATIVE EXAMPLE2 | LACTOBACILLUS BULGARICUS MB STRAIN | 5 | 42.4 | 12.5 | 81.7 |
| INVENTIVE EXAMPLE4 | | 2.5 | 52.4 | 18.0 | 93.0 |
| INVENTIVE EXAMPLE5 | | 1 | 59.3 | 26.5 | 93.0 |
| INVENTIVE EXAMPLE6 | | 0 | 69.6 | 41.0 | 80.0 |

LACTOSE CONCENTRATION (% BY MASS): MEASUREMENT VALUE OF RAW MATERIAL MILK BEFORE FERMENTATION STARTS

CONTENT OF EPS, COUNT OF LACTOBACILLUS BULGARICUS, COUNT OF STREPTOCOCCUS THERMOPHILUS: MEASUREMENT VALUE OF FERMENTED MILK (RAW MATERIAL MILK THAT HAS BEEN FERMENTED)

(56) References Cited

U.S. PATENT DOCUMENTS

| | | |
|---|---|---|
| 2017/0135360 A1 | 5/2017 | Garrigues et al. |
| 2018/0139977 A1 | 5/2018 | Morie et al. |

FOREIGN PATENT DOCUMENTS

| | | |
|---|---|---|
| JP | 2017-522012 A | 8/2017 |
| SG | 11201400553Q A | 6/2014 |
| SG | 11201503729Q A | 6/2015 |
| WO | 2012026384 A1 | 3/2012 |
| WO | WO 2013/039188 A1 | 3/2013 |
| WO | WO 2014/084340 A1 | 6/2014 |
| WO | 2016/009951 A1 | 1/2016 |
| WO | WO 2016/186151 A1 | 11/2016 |

OTHER PUBLICATIONS

O'Leary et al., Utilization of Lactose, Glucose, and Galactose by a Mixed Culture of *Streptococcus thermophilus* and Lactobacillus bulgaricus in Milk Treated with Lactase Enzyme, Applied Environmental Microbiology, Jul. 1976, pp. 89-94. (Year: 1976).*

Makino et al., Application of exopolysaccharides (EPS) produced from *Lactobacillus delbrueckii* ssp. *bulgaricus*, and studies on increasing the production of EPS, Japanese Journal of Lactic Acid Bacteria, Jan. 2013, 24(1):10-17. (Year: 2013).*

International Search Report for corresponding International Application No. PCT/JP2018/035502 mailed Nov. 13, 2018.

O'Leary, V.S. and Woychik, J.H.: Utilization of Lactose, Glucose, and Galactose by a Mixed Culture of *Streptococcus thermophilus* and Lactobacillus bulgaricus in Milk Treated with Lactase Enzyme, Appl. Environ. Microbiol., 1976, vol. 32, No. 1, pp. 89-94.

Makino, S. and Ikegami, S.: Application of exopolysaccharides (EPS) produced from *Lactobacillus delbrueckii* ssp. *bulgaricus*, and studies on increasing the production of EPS, Jpn. J. Lactic Acid Bact., 2013, vol. 24, No. 1, pp. 10-17; < w/ English Machine Translation>.

Yamamoto, E. et al.: Analysis of the effect of lactose degradation of the medium on the growth of LB81 starter, Aug. 7, 2018, vol. 70th, p. 194, 2Jp11 <w/ English Machine Translation>.

Zhennai Yang: "Antimicrobial Compounds and Extracellular Polysaccharides Produced By Lactic Acid Bacteria: Structures and Properties", Academic Dissertation Mar. 24, 2000, pp. 1-61.

Makino et al: "Immunomodulatory effects of polysaccharides produced by *Lactobacillus delbrueckii* ssp. *bulgaricus* OLL1073R-1", Journal of Dairy Science, American Dairy Science Association, US vol. 89, No. 8, Jan. 1, 2006, pp. 2873-2881.

C. Schmidt et al., "Fermented milk products: effects of lactose hydrolysis and fermentation conditions on the rheological properties", Dairy Science & Technology; (2016) vol. 96; pp. 199-211.

Science and Technique of Lactic Acid Bacterium (1966, Lactic Acid Bacterium study meeting, Issuer: Yoshida Shinji, Publishing house: Academic Publish Center) and partial English translation.

H. Douglas Goff, et al: "17. Microorganisms in Milk", Dairy Science and Technology ebook, https://www.uoguelph.ca/foodscience/book/, 2009.

Kilara Journal of Dairy Science vol. 59, No. 12, 2031-2035. (Year: 1976).

Nagaraj et al, "Standardization of different levels of lactose hydrolysis in the preparation of lactose hydrolyzed yoghurt", Iranian Journal of Veterinary Research, Shiraz University, vol. 10, No. 2. Ser. No. 27, 2009.

Makino et al.; "Enhanced natural killer cell activation by exopolysaccharides derived from yogurt fermented with *Lactobacillus delbrueckii* ssp. *bulgaricus* OLL1073R-1"; Journal of Dairy Science, American Dairy Science Association, US vol. 99, No. 2; 2016.

* cited by examiner

| | LACTIC ACID BACTERIUM STARTER | LACTOSE CONCENTRATION (% BY MASS) | CONTENT OF EPS (mg/kg) | COUNT OF LACTOBACILLUS BULGARICUS ($\times 10^7$ cfu/g) | COUNT OF STREPTOCOCCUS THERMOPHILUS ($\times 10^7$ cfu/g) |
|---|---|---|---|---|---|
| COMPARATIVE EXAMPLE1 | OLL1073R-1 STRAIN | 5 | 23.6 | 21.2 | 66.0 |
| INVENTIVE EXAMPLE1 | | 2.5 | 26.2 | 24.7 | 95.5 |
| INVENTIVE EXAMPLE2 | | 1 | 31.6 | 25.3 | 103.5 |
| INVENTIVE EXAMPLE3 | | 0 | 36.5 | 37.9 | 80.5 |
| COMPARATIVE EXAMPLE2 | LACTOBACILLUS BULGARICUS MB STRAIN | 5 | 42.4 | 12.5 | 81.7 |
| INVENTIVE EXAMPLE4 | | 2.5 | 52.4 | 18.0 | 93.0 |
| INVENTIVE EXAMPLE5 | | 1 | 59.3 | 26.5 | 93.0 |
| INVENTIVE EXAMPLE6 | | 0 | 69.6 | 41.0 | 80.0 |

LACTOSE CONCENTRATION (% BY MASS) : MEASUREMENT VALUE OF RAW MATERIAL MILK BEFORE FERMENTATION STARTS

CONTENT OF EPS

COUNT OF LACTOBACILLUS BULGARICUS } : MEASUREMENT VALUE OF FERMENTED MILK (RAW MATERIAL MILK THAT HAS BEEN FERMENTED)

COUNT OF STREPTOCOCCUS THERMOPHILUS

FERMENTED MILK AND METHOD FOR MANUFACTURING FERMENTED MILK

TECHNICAL FIELD

The present invention relates to fermented milk and a production method of the fermented milk. More specifically, the present invention relates to fermented milk in which an amount of polysaccharides generated by a lactic acid bacterium is controlled and a production method of fermented milk with which an amount of polysaccharides generated by a lactic acid bacterium is controlled.

BACKGROUND ART

Fermented milk is produced by fermentation of raw material milk to which a lactic acid bacterium starter is added. A lactic acid bacterium such as *Lactobacillus bulgaricus* or *Streptococcus thermophilus* is used as a lactic acid bacterium starter. Many strains that generate exopolysaccharide (EPS) are present among lactic acid bacteria.

EPS has been known to not only contribute to the stability of fermented milk but also provide effects of probiotics when being ingested into a human body. For example, it has been known that EPS generated by an OLL1073R-1 strain (a *Lactobacillus delbruechii* subsp. *bulgaricus* OLL1073R-1 strain), which is a type of *Lactobacillus bulgaricus*, has an effect of preventing autoimmune diseases. It has been known that fermented milk produced using the OLL1073R-1 strain has effects such as activation of NK cells and reduction of common cold.

In this manner, it is possible to provide functional food that contributes to health by utilizing a lactic acid bacterium that generates EPS and EPS generated by the lactic acid bacterium. It is necessary to increase an amount of EPS included in functional food in order to efficiently produce such functional food.

Patent Document 1 discloses a production method of fermented milk that enables an increase in amount of EPS to be generated by fermentation of raw material milk to which phosphate is added. Phosphate functions as a pH buffer in fermented milk. Phosphate can extend the period of time in which raw material milk is in a pH range where a lactic acid bacterium can grow during fermentation of the raw material milk, so that the amount of EPS that is to be generated and derived from lactic acid bacterium can be increased.

[Patent Document 1] WO 2014/84340 A1

SUMMARY OF THE INVENTION

Problems to be Solved by the Invention

An object of the present disclosure is to provide fermented milk including a large amount of EPS and a production method of fermented milk that enables an increase in amount of EPS to be generated.

Means for Solving the Problems

The fermented milk according to the present disclosure is produced by fermentation of raw material milk. Before fermentation of the raw material milk starts, the lactose concentration in the raw material milk is not more than 2.5% by mass with respect to the total amount of the raw material milk.

In the fermented milk according to the present disclosure, the lactose concentration in the fermented milk may be not more than 1.25% by mass with respect to the total amount of the fermented milk.

In the fermented milk according to the present disclosure, the amount of EPS may be not less than 1.05 times and not more than 4.2 times of the content of EPS in the fermented milk obtained by fermentation of raw material milk without degradation of lactose included in the raw material milk.

The fermented milk according to the present disclosure may contain *Lactobacillus bulgaricus*. The count of *Lactobacillus bulgaricus* included in the fermented milk may be not less than 1.08 times and not more than 4.7 times of the count of *Lactobacillus bulgaricus* included in the fermented milk obtained by fermentation of raw material milk without degradation of lactose included in the raw material milk.

The fermented milk according to the present disclosure may contain an OLL1073R-1 strain which is *Lactobacillus bulgaricus* and not less than 25 (mg/kg) and not more than 100 (mg/kg) of EPS.

The production method of fermented milk according to the present disclosure includes a preparation step, a lactose degradation step and a fermentation step. In the preparation step, raw material milk is prepared. In the lactose degradation step, at least part of lactose included in the prepared raw material milk is degraded using a lactose-degrading enzyme. In the fermentation step, a lactic acid bacterium is added to the raw material milk in which at least part of lactose is degraded, and the raw material milk to which the lactic acid bacterium is added is fermented. The lactose concentration in the raw material milk in which lactose is degraded is not more than 2.5% by mass with respect to the total amount of the raw material milk.

Effects of the Invention

The fermented milk according to the present invention can contain more EPS than conventional fermented milk. Further, the production method of fermented milk according to the present invention can increase an amount of EPS to be generated by a lactic acid bacterium starter added to the raw material milk.

BRIEF DESCRIPTION OF THE DRAWINGS

FIG. 1 is a table showing the content of EPS, the count of *Lactobacillus bulgaricus* and the count of *Streptococcus thermophilus* in fermented milk according to inventive examples 1 to 6 of the present invention.

EMBODIMENTS FOR CARRYING OUT THE INVENTION

Embodiments of the present invention will be described below in detail.

1. Lactose Concentration in Raw Material Milk

The fermented milk according to the present embodiment is produced by fermentation of raw material milk. The fermented milk according to the present embodiment is the raw material milk that has been fermented. For production of the fermented milk according to the present embodiment, the raw material milk in which lactose is degraded before fermentation starts is used. The lactose concentration in the raw material milk before fermentation starts is preferably not more than 2.5% by mass with respect to the total amount of the raw material milk.

Before fermentation starts, lactose included in the raw material milk is degraded such that the lactose concentration becomes not more than 2.5% by mass. Therefore, the amount of EPS and the count of *Lactobacillus bulgaricus* included in the fermented milk according to the present embodiment can be increased to be larger than those included in the conventional fermented milk obtained by fermentation of raw material milk in which lactose is not degraded. EPS refers to exopolysaccharide (EPS) generated by a lactic acid bacteria.

The lactose concentration in the raw material milk before fermentation starts is more preferably not more than 1% by mass. The fermented milk obtained by fermentation of the raw material milk having the lactose concentration of not more than 1% by mass before fermentation starts has more EPS and *Lactobacillus bulgaricus* than the conventional fermented milk.

The lactose concentration in the raw material milk before fermentation starts is even more preferably 0% by mass. The fermented milk obtained by fermentation of the raw material milk having the lactose concentration of 0% by mass before fermentation starts has even more EPS and *Lactobacillus bulgaricus* than the conventional fermented milk. The lactose concentration being 0% by mass means that lactose is not detected in the raw material milk or the fermented milk. The method of detecting lactose included in the raw material milk or the fermented milk is not particularly limited, and a conventionally known method can be used.

2. Definition of Fermented Milk

The fermented milk according to the present embodiment is fermented milk and a lactic acid bacterium beverage defined by the Ministerial Ordinance on Milk and Milk products concerning compositional standards (Dec. 27, 1951, Ministry of Health and Welfare No. 52). The fermented milk defined in the Ministerial Ordinance refers to a paste or liquid that is obtained by fermentation of milk or milk including an amount of non-fat milk solids equal to or larger than non-fat milk solids in the milk with a lactic acid bacterium or yeast, or the product obtained when the paste or liquid is frozen. The lactic acid bacterium beverage defined in the Ministerial Ordinance is a product obtained when milk or the like is fermented with a lactic acid bacterium or yeast and then processed, or the beverage in which the above-mentioned product is used as a main ingredient.

The fermented milk according to the present embodiment includes at least *Lactobacillus bulgaricus* and *Streptococcus thermophilus* as lactic acid bacteria. This is because, according to the United Nations Food and Agriculture Organization (FAO) and the World Health Organization (WHO), yogurt is defined to be made from milk and lactic acid bacteria that are used as raw materials, and is made from dairy products such as milk and powdered skimmed milk by the lactic acid fermentation action of both *Lactobacillus bulgaricus* and *Streptococcus thermophilus*.

In the present embodiment, "*Lactobacillus bulgaricus*" is a lactic acid bacterium of the species *Lactobacillus delbruechii* subsp. *bulgaricus*. "*Streptococcus thermophilus*" is a lactic acid bacterium of the species *Streptococcus thermophilus*.

The fermented milk according to the present embodiment may include a lactic acid bacterium other than *Lactobacillus bulgaricus* and *Streptococcus thermophilus*. The fermented milk according to the present embodiment may include *Lactobacillus gasseri*, *Bifidobacterium* and the like. *Lactobacillus gasser* is a lactic acid bacterium of the species *Lactobacillus gasseri*. Bifidobacteria is a lactic acid bacterium of the species *Bifidobacterium bifidum*.

In the following description, the fermented milk according to the present embodiment (the fermented milk that is produced from the raw material milk having the lactose concentration of not more than 2.5% by mass before fermentation starts) is simply referred to as "fermented milk" unless otherwise specified.

3. Lactose Concentration in Fermented Milk

Fermented milk is obtained by fermentation of the raw material milk having the lactose concentration of not more than 2.5% by mass before fermentation starts. During the period of time in which the raw material milk is fermented, the lactose included in the raw material milk is consumed by *Lactobacillus bulgaricus* and *Streptococcus thermophilus*. Therefore, the lactose concentration in the fermented milk is lower than that in the raw material milk, and is preferably not more than 1.25% by mass with respect to the total amount of the fermented milk. The lactose concentration in the fermented milk is more preferably 0% by mass with respect to the total amount of the fermented milk.

4. Content of EPS and Count of *Lactobacillus Bulgaricus* in Fermented Milk

The content of EPS and the count of *Lactobacillus bulgaricus* in the fermented milk according to the present embodiment will be specifically described below.

The fermented milk according to the present embodiment contains more EPS than the conventional fermented milk produced from the raw material milk having the lactose concentration of higher than 2.5% by mass before fermentation starts. Hereinafter, the conventional fermented milk produced from the raw material milk having the lactose concentration of higher than 2.5% by mass before fermentation starts is referred to as "conventional fermented milk."

Specifically, the fermented milk according to the present embodiment preferably contains EPS in an amount of not less than 1.06 times and not more than 4.2 times of EPS contained in the conventional fermented milk. The fermented milk according to the present embodiment more preferably contains EPS in an amount of not less than 1.27 times and not more than 4.2 times of EPS contained in the conventional fermented milk. The fermented milk according to the present embodiment even more preferably contains EPS in an amount of not less than 1.48 times and not more than 4.2 times of EPS contained in the conventional fermented milk. Here, a unit for the content of EPS in the fermented milk is "mg/kg".

The fermented milk according to the present embodiment contains more *Lactobacillus bulgaricus* than the conventional fermented milk. Specifically, the fermented milk according to this embodiment preferably contains *Lactobacillus bulgaricus* in an amount of not less than 1.08 times and not more than 4.7 times of *Lactobacillus bulgaricus* contained in the conventional fermented milk. The fermented milk according to the present embodiment more preferably contains *Lactobacillus bulgaricus* not in an amount of not less than 1.18 times and not more than 4.7 times of *Lactobacillus bulgaricus* contained in the conventional fermented milk. The fermented milk according to the present embodiment more preferably contains *Lactobacillus bulgaricus* in an amount of not less than 1.65 times and not more than 4.7 times of *Lactobacillus bulgaricus* contained in the conventional fermented milk. Here, the unit for the count of *Lactobacillus bulgaricus* is ($\times 10^7$ cfu/g).

(Content of EPS and Count of *Lactobacillus Bulgaricus* According to Production Condition)

The content of EPS and the count of *Lactobacillus bulgaricus* in the fermented milk according to the present embodiment change according to a production condition. First to sixth conditions will be mentioned below as the production conditions, and the content of EPS and the count of *Lactobacillus bulgaricus* in the fermented milk that is produced under each condition will be described below in further detail.

The *Lactobacillus bulgaricus* separated from Meiji Probio Yogurt R-1 (manufactured by Meiji Co., Ltd.) is used as a lactic acid bacterium starter under the first to third conditions. The *Lactobacillus bulgaricus* separated from Meiji Bulgarian Yogurt LB81 (manufactured by Meiji Co., Ltd.) is used as a lactic acid bacterium starter under the fourth to sixth conditions.

Here, the *Lactobacillus bulgaricus* separated from Meiji Probio Yogurt R-1 is a *Lactobacillus delbruechii* subsp. *bulgaricus* OLL1073R-1 strain and is deposited under depositary number FERM BP-10741 at the International Patent Organism Depositary, National Institute of Advanced Industrial Science and Technology. In the following description, the *Lactobacillus bulgaricus* separated from Meiji Probio yogurt R-1 is referred to as the "OLL1073R-1 strain." The *Lactobacillus bulgaricus* separated from Meiji Bulgarian Yogurt LB81 is referred to as a "*Lactobacillus bulgaricus* MB strain."

(First to Third Conditions)

Under the first condition, the OLL1073R-1 strain is added to the raw material milk having the lactose concentration of not more than 2.5% by mass before fermentation starts for production of fermented milk.

The content of EPS in the fermented milk produced under the first condition is not less than 25 (mg/kg) or not more than 100 (mg/kg). The fermented milk produced under the first condition contains EPS in an amount of not less than 1.06 times and not more than 4.2 times of EPS contained in the conventional fermented milk in which the OLL1073R-1 strain is used. Here, the upper limit "100 (mg/kg)" for the content of EPS is the value indicating the content of EPS that is assumed to be generated in a case where a lactic acid bacterium consumes all of the sugar included in the fermented milk.

The count of *Lactobacillus bulgaricus* in the fermented milk produced under the first condition is not less than 23 ($\times 10^7$ cfu/g) and not more than 100 ($\times 10^7$ cfu/g). The fermented milk produced under the first condition contains *Lactobacillus bulgaricus* in an amount of not less than 1.08 times and not more than 4.7 times of *Lactobacillus bulgaricus* contained in the conventional fermented milk in which the OLL1073R-1 strain is used.

Under the second condition, the OLL1073R-1 strain is added to the raw material milk having the lactose concentration of not more than 1% by mass before fermentation starts for production of fermented milk. That is, the lactose concentration in the raw material milk produced under the second condition is lower than that in the raw material milk produced under the first condition.

The fermented milk produced under the second condition contains EPS in an amount of not less than 30 (mg/kg) and not more than 100 (mg/kg). The fermented milk produced under the second condition contains EPS in an amount of not less than 1.27 times and not more than 4.2 times of EPS contained in the conventional fermented milk in which the OLL1073R-1 strain is used.

Further, the fermented milk produced under the second condition has *Lactobacillus bulgaricus* in an amount of not less than 25 ($\times 10^7$ cfu/g) and not more than 100 ($\times 10^7$ cfu/g). The fermented milk produced under the second condition contains *Lactobacillus bulgaricus* in an amount of not less than 1.18 times and not more than 4.7 times of *Lactobacillus bulgaricus* contained in the conventional fermented milk in which the OLL1073R-1 strain is used.

The third condition is that the OLL1073R-1 strain is added to the raw material milk having the lactose concentration of 0% by mass before fermentation starts for production of fermented milk. That is, the lactose concentration in the raw material milk produced under the third condition is lower than that in the raw material milk produced under the first condition and the second condition.

The fermented milk produced under the third condition contains EPS in an amount of not less than 35 (mg/kg) and not more than 100 (mg/kg). The fermented milk produced under the third condition contains EPS in an amount of not less than 1.48 times and not more than 4.2 times of EPS in the conventional fermented milk in which the OLL1073R-1 strain is used.

Further, the fermented milk produced under the third condition has *Lactobacillus bulgaricus* in an amount of not less than 35 ($\times 10^7$ cfu/g) and not more than 100 ($\times 10^7$ cfu/g). The fermented milk produced under the third condition contains *Lactobacillus bulgaricus* in an amount of not less than 1.65 times and not more than 4.7 times of *Lactobacillus bulgaricus* contained in the conventional fermented milk in which the "OLL1073R-1" strain is used.

(4th to 6th Conditions)

The fourth condition is that the *Lactobacillus bulgaricus* MB strain is added to the raw material milk having the lactose concentration of not more than 2.5% by mass before fermentation starts for production of fermented milk.

The fermented milk produced under the fourth condition contains EPS in an amount of is not less than 50 (mg/kg) and not more than 100 (mg/kg). The fermented milk produced under the fourth condition contains EPS in an amount of not less than 1.18 times and not more than 2.36 times of EPS in the conventional fermented milk in which the *Lactobacillus bulgaricus* MB strain is used.

Further, the fermented milk produced under the fourth condition has *Lactobacillus bulgaricus* in an amount of not less than 15 ($\times 10^7$ cfu/g) and not more than 100 ($\times 10^7$ cfu/g). The fermented milk produced under the fourth condition contains *Lactobacillus bulgaricus* in an amount of not less than 1.2 times and not more than 8.0 times of *Lactobacillus bulgaricus* contained in the fermented milk in which the *Lactobacillus bulgaricus* MB strain is used.

The fifth condition is that the *Lactobacillus bulgaricus* MB strain is added to the raw material milk having the lactose concentration of not more than 1% by mass before fermentation starts for production of fermented milk. That is, the lactose concentration in the raw material milk produced under the fifth condition is lower than that in the raw material milk produced under the fourth condition.

The fermented milk produced under the fifth condition contains EPS in an amount of not less than 55 (mg/kg) and not more than 100 (mg/kg). The fermented milk produced under the fifth condition contains EPS in an amount of not less than 1.3 times and not more than 2.36 times of EPS contained in the conventional fermented milk in which the *Lactobacillus bulgaricus* MB strain is used.

The fermented milk produced under the fifth condition has *Lactobacillus bulgaricus* in an amount of not less than 25 ($\times 10^7$ cfu/g) and not more than 100 ($\times 10^7$ cfu/g). The fermented milk produced under the fifth condition has *Lactobacillus bulgaricus* in an amount of not less than 2.0 times and not more than 8.0 times of *Lactobacillus bulgaricus* in the conventional fermented milk that is produced by addition of the *Lactobacillus bulgaricus* MB strain to the raw material milk having the lactose concentration of larger than 2.5% by mass before fermentation starts.

The sixth condition is that the *Lactobacillus bulgaricus* MB strain is added to the raw material milk having the lactose concentration of 0% by mass before fermentation starts for production of fermented milk. That is, the lactose concentration in the raw material milk produced under the sixth condition is lower than that in the raw material milk produced under the fourth condition and the fifth condition.

The fermented milk produced under the sixth condition contains EPS in an amount of not less than 65 (mg/kg) and not more than 100 (mg/kg). The fermented milk produced under the sixth condition contains EPS in an amount of not less than 1.53 times and not more than 2.36 times of EPS contained in the conventional fermented milk in which the *Lactobacillus bulgaricus* MB strain is used.

Further, the fermented milk produced under the sixth condition has *Lactobacillus bulgaricus* in an amount of not less than 40 ($\times 10^7$ cfu/g) and not more than 100 ($\times 10^7$ cfu/g). The fermented milk produced under the sixth condition contains *Lactobacillus bulgaricus* in an amount of not less than 3.2 times and not more than 8.0 times of *Lactobacillus bulgaricus* contained in the conventional fermented milk in which the *Lactobacillus bulgaricus* MB strain is used.

5. Production Method of Fermented Milk

The production method of fermented milk according to the present embodiment will be described below in detail.

5.1 Preparation Step

In a preparation step, raw material milk is prepared. For example, raw materials used for preparing raw material milk include water, raw milk, powdered skim milk, powdered whole milk, buttermilk, butter, cream, whey protein concentrate (WPC), whey protein isolate (WPI), α-lactalbumin and β-lactoglobulin or the like.

The raw material milk may only include a milk component for lactic acid fermentation to be carried out by a lactic acid bacterium. Therefore, the raw material milk does not have to include all the raw materials listed above, and raw materials other than the raw materials listed above may be used. The raw material milk is prepared by a conventionally known method. For example, the raw materials listed above are mixed to produce a mixture and the produced mixture is homogenized, whereby the raw material milk can be prepared. The raw material milk prepared in this manner includes lactose. Lactose is included in milk-derived raw materials such as raw milk, powdered skim milk and powdered whole milk.

5.2. Lactose Degradation Step

In the lactose degradation step, lactase is added to the prepared raw material milk, and at least part of lactose included in the prepared raw material milk is degraded by lactase. Lactase degrades lactose to produce glucose and galactose. The type of lactase to be added is not particularly limited as long as the optimal pH of lactase to be added is in a neutral range or an acidic range. For example, commercially available lactase can be added to the raw material milk.

The raw material milk to which lactase is added is kept in a temperature range of not less than 0° C. and not more than 50° C., for example, whereby degradation of lactose by lactase can be promoted. Lactose included in the raw material milk preferably continues to be degraded by lactase until the lactose concentration in the raw material milk becomes not more than 2.5% by mass. In a case where the lactose concentration in the raw material milk prepared in the preparation step is 5% by mass, for example, lactose continues to be degraded by lactase until the lactose degradation rate becomes not less than 50%.

Lactose included in the raw material milk more preferably continues to be degraded by lactase until the lactose concentration in the raw material milk becomes not more than 1% by mass. In a case where the lactose concentration in the raw material milk prepared in the preparation step is 5% by mass, for example, lactose continues to be degraded by lactase until the lactose degradation rate becomes not less than 80%.

Lactose included in the raw material even more preferably continues to be degraded by lactase until the lactose concentration in the raw material milk becomes 0% by mass. In this case, lactose continues to be degraded by lactase until the lactose degradation rate becomes 100% regardless of the lactose concentration in the raw material milk prepared in the preparation step.

Lactose is degraded by lactase by the time fermentation of the raw material milk by *Lactobacillus bulgaricus* and *Streptococcus thermophilus* starts. Fermentation starts when the lactic acid bacterium starters (*Lactobacillus bulgaricus* and *Streptococcus thermophilus*) are added to the raw material milk, for example.

5.3. Sterilization Step

In the sterilization step, the raw material milk in which lactose is degraded by lactase is heated to be sterilized. Heat sterilization of the raw material milk can be carried out by a conventionally known method. The lactase added to the raw material milk can be inactivated by heat sterilization of the raw material milk.

The sterilization step may be carried out before the lactose degradation step. In this case, because degradation of lactose by lactase can continue in a fermentation step, described below, the lactose concentration in the fermented milk can further be reduced.

5.4. Fermentation Step

The lactic acid bacterium starters are added to the sterilized raw material milk, and the raw material milk is fermented under a predetermined fermentation condition. The fermented raw material milk is refrigerated as the fermented milk according to the present embodiment.

The fermentation conditions such as a fermentation temperature and a fermentation period of time may be suitably adjusted in consideration of the type of a lactic acid bacterium starter added to raw material milk, a desired flavor of fermented milk, etc. Fermentation by the lactic acid bacteria can be promoted by placement of the raw material milk in an environment of not less than 30° C. and not more than 50°

C., for example. The fermentation period of time is suitably adjusted according to a fermentation temperature, the type of a lactic acid bacterium starter added to raw material milk, the desired acidity of lactic acid in fermented milk, etc.

As described above, with the production method of fermented milk according to the present embodiment, the lactose included in the raw material milk is degraded such that the lactose concentration in the raw material milk is not more than 2.5% by mass before fermentation starts, and the raw material milk in which lactose is degraded is fermented. The raw material milk produced in this manner can contain more EPS than the conventional fermented milk.

In the above-mentioned embodiment, it was defined that fermentation in the raw material milk started when the lactic acid bacterium starters were added to the raw material milk. However, since the count of lactic acid bacteria starters added to the raw material milk does not increase in an induction period (the period until the logarithmic growth phase starts), lactose is hardly consumed in the induction period. Therefore, it can be defined that fermentation starts when the logarithmic growth phase of lactic acid bacteria starts. In this case, the sterilization step is carried out before the lactose degradation step. That is, lactase is added to the heat sterilized raw material milk. In a case where fermentation is to start when the logarithmic growth phase starts, degradation of lactose by lactase continues even after the lactic acid bacterium starters are added to the raw material milk. The lactose concentration in the raw material milk may only be not more than 1.5% by mass when the logarithmic growth phase starts.

INVENTIVE EXAMPLES

Each inventive example will be described below. However, the present invention is not limited to each inventive example, described below.

Inventive Example 1

Fermented milk according to an inventive example 1 corresponds to the fermented milk produced under the above-mentioned first condition.

500.0 g of raw milk, 53.2 g of powdered skim milk, 23.0 g of fresh cream and 403.6 g of tap water were mixed for preparation of raw material milk. The lactose concentration in the prepared raw material milk was 5% by mass. This prepared raw material milk was cooled to 5° C. and then 0.2 g of lactase (GODO-YNL, manufactured by Godo Shusei Co., Ltd.) was added to the raw material milk, whereby lactose included in the raw material milk was degraded. Specifically, degradation of lactose continued until the lactose degradation rate in the raw material milk became 50%. A measurement method of lactose degradation rate will be described below. The lactose concentration in the raw material milk in which lactose was degraded was 2.5% by mass. Thereafter, the raw material milk in which lactose was degraded was heat sterilized at the temperature of 95° C., and then the heat sterilized raw material milk was cooled to the temperature of 43° C.

The measurement method of lactose degradation rate in raw material milk will be described. First, the content of lactose per solid content in the raw material milk before lactase is added is measured. Next, the content of glucose per solid content in the raw material milk is measured based on the glucose concentration in the raw material milk in which lactose is degraded.

The lactose degradation rate is calculated by the following formula using the measured content of lactose and the measured content of glucose.

Lactose degradation rate (%)=[(the content of glucose×2)/the content of lactose]×100

The content of lactose can be measured using an arginine fluorescence method by high performance liquid chromatography (BUNSEKI KAGAKU, Volume 32, page E207, published by The Japan Society for Analytical Chemistry, 1983). The content of glucose can be measured using Medisafe Mini (manufactured by Terumo Corporation), for example. The lactose concentration can be calculated from the concentration of solid content and the content of lactose in the raw material milk.

Next, the lactic acid bacteria separated from Meiji Probio Yogurt R-1 (manufactured by Meiji Co., Ltd.) were added to the heat sterilized raw material milk as lactic acid bacterium starters. The lactic acid bacteria separated from Meiji Probio yogurt R-1 include *Streptococcus thermophilus* and the OLL1073R-1 strain that is *Lactobacillus bulgaricus*. The addition amount of the lactic acid bacterium starters is 20 g. A cup container (capacity: 100 mL, made of plastic) was filled with the raw material milk to which the lactic acid bacterium starters were added. Static fermentation of the raw material milk filling the cup container was carried out in a fermentation chamber at a temperature of 43° C. until the acidity of lactic acid became 0.7%.

The statically fermented raw material milk in the cup was cooled in a refrigerator at 10° C. as the fermented milk according to the inventive example 1. The lactose concentration in the fermented milk according to the inventive example 1 immediately after fermentation ended was 1.25% by mass.

Further, the content of EPS, the count of *Lactobacillus bulgaricus* and the count of *Streptococcus thermophilus* in the cooled fermented milk according to the inventive example 1 were measured.

The count of *Lactobacillus bulgaricus* and the count of *Streptococcus thermophilus* in the fermented milk can be measured by a conventionally known method. For example, a predetermined amount of fermented milk is suitably diluted, and a diluted solution of the fermented milk is smeared on a BL medium. Live bacteria smeared on the BL medium are anaerobically cultured for 72 hours in a temperature environment of 37° C., and the colonies on the BL medium after cultivation are measured, whereby the count of *Lactobacillus bulgaricus* and the count of *Streptococcus thermophilus* can be found.

The measurement method of the content of EPS in the fermented milk will be described. First, 10 g of the fermented milk according to the inventive example 1 was put into a tube having a capacity of 50 mL, and 1 mL of 100% trichloroacetic acid was added to the tube into which the fermented milk according to the inventive example 1 was put. The contents of the tube were agitated and the agitated contents were centrifuged at a relative centrifugal force of 12000 G. The supernatant obtained by centrifugation was transferred to a new tube having a capacity of 50 mL. Ethanol in an amount of twice the amount of the supernatant was added to the supernatant in the new tube while the supernatant in the new tube was agitated. The mixture of supernatant and ethanol was left in a stationary state overnight at a temperature of 4° C. The mixture that was left in a stationary state was centrifuged at a relative centrifugal force of 12000 G, and the supernatant was removed from the centrifuged mixture. 10 mL of purified water was added to the precipitate in the centrifuged mixture, and the precipitate was completely dissolved in the purified water. The purified water in which the precipitate was dissolved was injected into the high performance liquid chromatography (HPLC) using a syringe having a filter and a diameter of 0.45 μm. Then, the ratio of "the peak area of a single peak detected by an RI detector around the point in time at which 16 minutes has elapsed since the point in time at which injection was started" to "the total peak area" represented the content of EPS in the inventive example 1.

The analysis conditions of HPLC are as follows.
HPLC system: ACQUITY UPLC H-Class (Waters)
Column: OHpak SB-806HQ, SB-G (Shodex)
Temperature of column: 40° C.
Solvent: 0.2M NaCl aqueous solution
Flow rate: 0.5 mL/min
Detector: RI detector 2414 (Waters)
Detection temperature: 40° C.
Sample injection: 150 μL
Analysis period of time: 50 min Inventive Example 2

Fermented milk according to an inventive example 2 corresponds to the fermented milk produced under the above-mentioned second condition. The fermented milk according to the inventive example 2 is the same as the fermented milk according to the above-mentioned inventive example 1 except that the lactose included in the raw material milk continues to be degraded by lactase until the lactose degradation rate becomes 80%. The lactose concentration in the raw material milk according to the inventive example 2 was 1% by mass before fermentation started. The lactose concentration in the fermented milk according to the inventive example 2 was 0% by mass immediately after fermentation ended. That is, lactose was not detected from the fermented milk according to the inventive example 2 immediately after fermentation ended.

Inventive Example 3

Fermented milk according to an inventive example 3 corresponds to the fermented milk produced under the above-mentioned third condition. A production process of the fermented milk according to the inventive example 3 is the same as that of the fermented milk according to the above-mentioned inventive example 1 except that the lactose included in the raw material milk continues to be degraded by lactase until the lactose degradation rate becomes 100%. The lactose concentration in the raw material milk according to the inventive example 3 was 0% by mass before fermentation started. The lactose concentration in the fermented milk according to the inventive example 3 was 0% by mass immediately after fermentation ended. That is, lactose was not detected from the fermented milk according to the inventive example 3 before fermentation started or immediately after fermentation ended.

Comparative Example 1

Fermented milk according to a comparative example 1 corresponds to the conventional fermented milk in which the OLL1073R-1 strain is used.

In the production process of the fermented milk according to the comparative example 1, the lactose degradation step is removed from the production method in the inventive example 1. The lactose degradation rate in the raw material milk according to the comparative example 1 was 0% by mass, and the lactose concentration in the raw material milk according to the comparative example 1 was 5% by mass before fermentation started. The lactose concentration in the fermented milk according to the comparative example 1 was 3.75% by mass immediately after fermentation ended.

Inventive Example 4

Fermented milk according to an inventive example 4 corresponds to the fermented milk produced under the above-mentioned fourth condition. The production process of the fermented milk according to the inventive example 4 is the same as that of the fermented milk according to the inventive example 1 except that the lactic acid bacterium starter is not the OLL1073R-1 strain but the *Lactobacillus bulgaricus* MB strain. The lactose concentration in the raw material milk according to the inventive example 4 was 2.5% by mass before fermentation started. The lactose concentration in the fermented milk according to the inventive example 4 was 1.25% by mass immediately after fermentation ended.

Inventive Example 5

Fermented milk according to an inventive example 5 corresponds to the fermented milk produced under the above-mentioned fifth condition. The production process of the fermented milk according to the inventive example 5 is the same as that of the fermented milk according to the inventive example 2 except that the lactic acid bacterium starter is not the OLL1073R-1 strain but the *Lactobacillus bulgaricus* MB strain. The lactose concentration in the raw material milk according to the inventive example 5 was 1% by mass before fermentation started. The lactose concentration in the fermented milk according to the inventive example 5 was 0% by mass immediately after fermentation ended. That is, lactose was not detected from the fermented milk according to the inventive example 5 immediately after fermentation ended.

Inventive Example 6

Fermented milk according to an inventive example 6 corresponds to the fermented milk produced under the above-mentioned sixth condition. The production process of the fermented milk according to the inventive example 6 is the same as that of the fermented milk according to the inventive example 3 except that the lactic acid bacterium starter is not the OLL1073R-1 strain but the *Lactobacillus bulgaricus* MB strain. The lactose concentration in the raw material milk according to the inventive example 6 was 0% by mass before fermentation started. The lactose concentration in the fermented milk according to the inventive example 6 was 0% by mass immediately after fermentation ended. That is, lactose was not detected from the fermented milk according to the inventive example 6 before fermentation started and immediately after fermentation ended.

Comparative Example 2

Fermented milk according to a comparative example 2 corresponds to the conventional fermented milk in which the *Lactobacillus bulgaricus* MB strain is used. The production process of the fermented milk according to the comparative example 2 is the same as that of the fermented milk according to the comparative example 1 except that the lactic acid bacterium starter is not the OLL1073R-1 strain but the *Lactobacillus bulgaricus* MB strain. The lactose degradation rate in the raw material milk according to the comparative example 2 was 0%, and the lactose concentration in the raw material milk according to the comparative example 2 was 5% by mass before fermentation started. The lactose concentration in the fermented milk according to the comparative example 2 was 3.75% by mass immediately after fermentation ended.

Study

FIG. 1 is a table showing the content of EPS, the count of *Lactobacillus bulgaricus* and the count of *Streptococcus thermophilus* in the fermented milk according to the inventive examples 1 to 6, and the comparative examples 1 and 2. The relationship between the lactose concentration in the raw material milk and the content of EPS in the fermented milk, and the relationship between the lactose concentration in the raw material milk and the count of *Lactobacillus bulgaricus* in the fermented milk will be described with reference to FIG. 1.

Relationship Between Lactose Concentration in Raw Material Milk and Content of EPS (In a Case Where the OLL1073R-1 Strain is the Lactic Acid Bacterium Starter)

In FIG. 1, reference is made to the content of EPS in each of the fermented milk of the inventive examples 1 to 3 and the comparative example 1. In a case where the OLL1073R-1 strain is the lactic acid bacterium starter, the lower the lactose concentration in the raw material milk before fermentation starts is, the larger the content of EPS is.

Specifically, in the comparative example 1, the lactose concentration in the raw material milk before fermentation starts is 5% by mass, and the content of EPS in the fermented milk is 23.6 (mg/kg). In the inventive example 1, the lactose concentration in the raw material milk before fermentation starts is 2.5% by mass, and the content of EPS in the fermented milk is 26.2 (mg/kg). In the inventive example 2, the lactose concentration in the raw material milk before fermentation starts is 1% by mass, and the content of EPS in the fermented milk is 31.6 (mg/kg). In the inventive example 3, the lactose concentration in the raw material milk before fermentation starts is 0% by mass, and the content of EPS in the fermented milk is 36.5 (mg/kg).

From the result of comparison between the inventive examples 1 to 3 and the comparative example 1, it was apparent that, in a case where the OLL1073R-1 strain was the lactic acid bacterium starter, it was possible to increase the content of EPS in the fermented milk by producing the fermented milk from the raw material milk having the lactose concentration of not more than 2.5% by mass before fermentation started.

(In a Case Where the *Lactobacillus bulgaricus* MB Strain is the Lactic Acid Bacterium Starter)

Referring to FIG. 1, reference is made to the content of EPS in each of the fermented milk of the inventive examples 4 to 6 and the comparative example 2. In a case where the *Lactobacillus bulgaricus* MB strain is the lactic acid bacterium starter, the lower the lactose concentration in the raw material milk before fermentation starts is, the larger the content of EPS is.

Specifically, in the comparative example 2, the lactose concentration in the raw material milk before fermentation starts is 5% by mass, and the content of EPS in the fermented milk is 42.4 (mg/kg). In the inventive example 4, the lactose concentration in the raw material milk before fermentation starts is 2.5% by mass, and the content of EPS in the fermented milk is 52.4 (mg/kg). In the inventive example 5, the lactose concentration in the raw material milk before fermentation starts is 1% by mass, and the content of EPS in the fermented milk is 59.3 (mg/kg). In the inventive example 6, the lactose concentration in the raw material milk before fermentation starts is 0% by mass, and the content of EPS in the fermented milk is 69.6 (mg/kg).

From the result of comparison between the inventive examples 4 to 6 and the comparative example 2, it was apparent that, in a case where the *Lactobacillus bulgaricus* MB strain was the lactic acid bacterium starter, it was possible to increase the content of EPS in the fermented milk by producing the fermented milk from the raw material milk having the lactose concentration of not more than 2.5% by mass before fermentation started.

That is, from the results of the inventive examples 1 to 6 and the comparative examples 1 and 2, it was apparent that it was possible to increase the content of EPS in the fermented milk efficiently by using *Lactobacillus bulgaricus* as the lactic acid bacterium starter and degrading lactose such that the lactose concentration in the raw material milk before fermentation started was not more than 2.5% by mass.

Relationship Between Lactose Concentration in Raw Material Milk and Count of *Lactobacillus Bulgaricus*

(In a Case Where the OLL1073R-1 Strain is the Lactic Acid Bacterium Starter)

Referring to FIG. 1, reference is made to the count of *Lactobacillus bulgaricus* in each of the fermented milk of the inventive examples 1 to 3 and the comparative example 1.

In the comparative example 1, the lactose concentration in the raw material milk before fermentation starts is 5% by mass, and the count of *Lactobacillus bulgaricus* in the fermented milk is 21.2 ($\times 10^7$ cfu/g). In the inventive example 1, the lactose concentration in the raw material milk before fermentation starts is 2.5% by mass, and the count of *Lactobacillus bulgaricus* in the fermented milk is 24.7 ($\times 10^7$ cfu/g). In the inventive example 2, the lactose concentration in the raw material milk before fermentation starts is 1% by mass, and the count of *Lactobacillus bulgaricus* in the fermented milk is 25.3 ($\times 10^7$ cfu/g). In the inventive example 3, the lactose concentration in the raw material milk before fermentation starts is 0% by mass, and the count of *Lactobacillus bulgaricus* in the fermented milk is 37.9 ($\times 10^7$ cfu/g).

In a case where the OLL1073R-1 strain is the lactic acid bacterium starter, the lower the lactose concentration in the raw material milk before fermentation starts is, the larger the count of *Lactobacillus bulgaricus* is. When the lactose concentration in the raw material milk before fermentation starts is the minimum (0% by mass), the count of *Lactobacillus bulgaricus* in the fermented milk is the maximum. It is considered that, in a case where lactose included in the raw material milk is degraded such that lactose concentration in the raw material milk before fermentation starts is not more than 2.5% by mass, the OLL1073R-1 strain included in the raw material milk is activated in the fermentation step, and EPS deprived from the OLL1073R-1 strain is efficiently generated.

In FIG. 1, reference is made to the count of *Streptococcus thermophilus* of the inventive examples 1 to 3 and the comparative example 1. The count of *Streptococcus thermophilus* in the fermented milk according to the inventive examples 1 to 3 is larger than that in the fermented milk according to the comparative example 1. That is, in a case where lactose in the raw material milk is degraded such that the lactose concentration in the raw material milk before fermentation starts is not more than 2.5% by mass, the count of *Streptococcus thermophilus* can be increased. However, since the count of *Streptococcus thermophilus* is the maximum in the inventive example 2 in which the lactose concentration in the raw material milk before fermentation starts is 1% by mass, the relationship between the lactose concentration and the count of *Streptococcus thermophilus* is not as clear as the relationship between the lactose concentration and the count of *Lactobacillus bulgaricus*. As described above, it is considered that, since the lower the lactose concentration in the raw material milk before fermentation starts is, the larger the count of *Lactobacillus bulgaricus* is, *Lactobacillus bulgaricus* contributes more to an increase in content of EPS than *Streptococcus thermophilus*.

In this manner, from the results of the inventive examples 1 to 3 and the comparative example 1, it was apparent that, in a case where the OLL1073R-1 strain was used as the lactic acid bacterium starter, it was possible to increase the content of EPS in the fermented milk by making the lactose concentration in the raw material milk before fermentation started be not more than 2.5% by mass.

(In a Case Where the *Lactobacillus bulgaricus* MB Strain is the Lactic Acid Bacterium Starter)

Referring to FIG. 1, reference is made to the count of *Lactobacillus bulgaricus* in each of the fermented milk of the inventive examples 4 to 6 and the comparative example 2.

In the comparative example 2, the lactose concentration in the raw material milk before fermentation starts is 5% by mass, and the count of *Lactobacillus bulgaricus* in the fermented milk is 12.5 ($\times 10^7$ cfu/g). In the inventive example 4, the lactose concentration in the raw material milk before fermentation starts is 2.5% by mass, and the count of *Lactobacillus bulgaricus* in the fermented milk is 18.0 ($\times 10^7$ cfu/g). In the inventive example 5, the lactose concentration in the raw material milk before fermentation starts is 1% by mass, and the count of *Lactobacillus bulgaricus* in the fermented milk is 26.5 ($\times 10^7$ cfu/g). In the inventive example 6, the lactose concentration in the raw material milk before fermentation starts is 0% by mass, and the count of *Lactobacillus bulgaricus* in the fermented milk is 41.0 ($\times 10^7$ cfu/g).

In a case where the *Lactobacillus bulgaricus* MB strain is the lactic acid bacterium starter, the lower the lactose concentration in the raw material milk before fermentation starts is, the higher the count of *Lactobacillus bulgaricus* is. When the lactose concentration in the raw material milk before fermentation starts is the minimum (0% by mass), the count of *Lactobacillus bulgaricus* in the fermented milk is the maximum. It is considered that, in a case where lactose included in the raw material milk is degraded such that lactose concentration in the raw material milk before fermentation starts is not more than 2.5% by mass, the *Lactobacillus bulgaricus* MB strain included in the raw material milk is activated in the fermentation step, and EPS deprived from the *Lactobacillus bulgaricus* MB strain is efficiently generated.

Reference is made to the count of *Streptococcus thermophilus* of the inventive examples 4 to 6 and the comparative example 2 in FIG. 1. The count of *Streptococcus thermophilus* in the fermented milk according to the inventive examples 4 to 6 is larger than that in the fermented milk according to the comparative example 2. That is, in a case where lactose in the raw material milk is degraded such that the lactose concentration in the raw material milk before fermentation starts is not more than 2.5% by mass, the count of *Streptococcus thermophilus* can be increased. However, the count of *Streptococcus thermophilus* is the maximum in the inventive examples 1 and 2 in which the lactose concentrations in the raw material milk before fermentation starts are 2.5% by mass and 1% by mass, respectively, the relationship between the lactose concentration and the count of *Streptococcus thermophilus* is not as clear as the relationship between the lactose concentration and the count of *Lactobacillus bulgaricus*. As described above, it is considered that, since the lower the lactose concentration in the raw material milk before fermentation starts is, the larger the count of *Lactobacillus bulgaricus* is, *Lactobacillus bulgaricus* contributes more to an increase in content of EPS than *Streptococcus thermophilus*.

In this manner, from the results of the inventive examples 4 to 6 and the comparative example 1, it was apparent that, in a case where the *Lactobacillus bulgaricus* MB strain was used as the lactic acid bacterium starter, it was possible to increase the content of EPS in the fermented milk by making the lactose concentration in the raw material milk before fermentation started be not more than 2.5% by mass.

From the results of the inventive examples 1 to 6 and the comparative examples 1 and 2, it was apparent that it was possible to generate EPS included in the fermented milk efficiently by using *Lactobacillus bulgaricus* as the lactic acid bacterium starter and degrading the lactose included in the raw material milk such that the lactose concentration in the raw material milk before fermentation started was not more than 2.5% by mass.

While the embodiments of the present invention have been described above, the above-mentioned embodiments are merely examples to show how to carry out the present invention. Accordingly, the present invention is not limited to the above-illustrated embodiments, and the above-illustrated embodiments can be modified as appropriate without departing the spirit of the present invention.

The invention claimed is:
1. A production method of fermented milk comprising:
 a preparation step of preparing raw material milk;
 a lactose degradation step of degrading at least part of lactose included in the raw material milk using a lactose-degrading enzyme; and
 a fermentation step of adding a lactic acid bacterium to the raw material milk in which the at least part of lactose is degraded and fermenting the raw material milk to which the lactic acid bacterium is added, wherein:
 a lactose concentration in the raw material milk in which lactose is degraded is not more than 2.5% by mass with respect to a total amount of the raw material milk; and
 a count of *Lactobacillus bulgaricus* in the fermented milk is not less than 23 ($\times 10^7$ cfu/g) and not more than 100 ($\times 10^7$ cfu/g).

2. The production method of fermented milk according to claim 1, wherein
 a lactose concentration in the fermented milk is not more than 1.25% by mass with respect to a total amount of the fermented milk.

3. The production method of fermented milk according to claim 1, wherein
  an amount of exopolysaccharide (EPS) is not less than 1.05 times and not more than 4.2 times of an amount of exopolysaccharide (EPS) contained in conventional fermented milk that is obtained by fermentation of the raw material milk without degradation of lactose included in the raw material milk.

4. The production method of fermented milk according to claim 1, further containing *Lactobacillus bulgaricus*, wherein
  a count of the *Lactobacillus bulgaricus* included in the fermented milk is not less than 1.08 times and not more than 4.7 times of a count of *Lactobacillus bulgaricus* included in conventional fermented milk obtained by fermentation of the raw material milk without degradation of lactose included in the raw material milk.

5. The production method of fermented milk according to claim 1, wherein
  the fermented milk contains:
    an OLL1073R-1 strain that is *Lactobacillus bulgaricus*, and
  not less than 25 (mg/kg) and not more than 100 (mg/kg) of exopolysaccharide (EPS).

* * * * *